United States Patent
Hoshika et al.

(10) Patent No.: US 7,198,690 B2
(45) Date of Patent: Apr. 3, 2007

(54) METHOD FOR CONTINUOUSLY MAKING DISPOSABLE DIAPER

(75) Inventors: Kazuhiko Hoshika, Mitoyo-gun (JP); Kaiyo Nakajima, Mitoyo-gun (JP); Yoshitaka Mishima, Mitoyo-gun (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/100,602

(22) Filed: Apr. 7, 2005

(65) Prior Publication Data
US 2005/0224171 A1 Oct. 13, 2005

(30) Foreign Application Priority Data
Apr. 7, 2004 (JP) ............................. 2004-112819

(51) Int. Cl.
  *B32B 37/00* (2006.01)
(52) U.S. Cl. ............. 156/250; 156/164; 156/229; 156/269
(58) Field of Classification Search .......... 156/160, 156/163, 164, 229, 250, 252, 264, 269, 494, 156/495, 510, 522
See application file for complete search history.

(56) References Cited

U.S. PATENT DOCUMENTS

| | | | |
|---|---|---|---|
| 3,943,930 A | 3/1976 | Schaar | |
| 4,557,777 A * | 12/1985 | Sabee | 156/201 |
| 6,527,893 B1 * | 3/2003 | Boisse et al. | 156/164 |
| 6,712,922 B2 * | 3/2004 | Sorenson et al. | 156/164 |
| 6,743,321 B2 * | 6/2004 | Guralski et al. | 156/250 |

FOREIGN PATENT DOCUMENTS

| | | |
|---|---|---|
| EP | 1216678 | 5/2003 |
| EP | 1234563 | 6/2004 |
| JP | 2002-315778 | 10/2002 |

OTHER PUBLICATIONS

Patent Abstracts of Japan—Publication No. 2002-315778, Published Oct. 29, 2002.
Patent Abstracts of Japan—Publication No. 2003-079664, Published Mar. 18, 2003.
Patent Abstracts of Japan—Publication No. 2002-345871, Published Dec. 3, 2002.

* cited by examiner

*Primary Examiner*—James Sells
(74) *Attorney, Agent, or Firm*—Lowe Hauptman & Berner LLP

(57) ABSTRACT

In a method for continuously making disposable diapers, first and second body fluid absorbent panels overlapping each other in a crotch region so as to form a feces retaining pocket are formed along transversely opposite side edges thereof with elastic leak-barrier cuffs. A pair of continuous leak-barrier cuffs are fed in the stretched state so that these continuous leak-barrier cuffs may partially cover the first and second body fluid absorbent panels overlapping each other in the crotch region. The transversely opposite side edges of these continuous cuffs are partially bonded to a partial region of a second inner surface of the second body fluid absorbent panel overlapping a first inner surface of the first body fluid absorbent panel.

16 Claims, 11 Drawing Sheets

METHOD FOR CONTINUOUSLY MAKING DISPOSABLE DIAPER

RELATED APPLICATIONS

The present application is based on, and claims priority from, Japanese Application Number 2004-112819, filed Apr. 7, 2004, the disclosure of which is hereby incorporated by reference herein in its entirety.

BACKGROUND OF THE INVENTION

This invention relates to a method for continuously making disposable diaper, more particularly disposable diaper formed with a feces retaining pocket.

The disposable diaper formed with the feces retaining pocket has already been well known. The disposable diaper disclosed in Japanese Unexamined Patent Application Publication No. 2002-315778 (Reference) is an example of such diaper formed with the feces retaining pocket. In this diaper of prior art, a body fluid absorbent first core is sandwiched between a liquid-pervious sheet and a liquid-impervious sheet to form a relatively large panel extending over a front waist region, a rear waist region and a crotch region. Such large panel is formed with a feces retaining depression. In this diaper, a relatively small panel comprising a body fluid absorbent second core covered with a liquid-pervious sheet is formed so as to overlap the front waist region and a part of the crotch region on the side of the inner surface of the diaper. This relatively small panel covers a part of the feces retaining depression of the relatively large panel in the crotch region so that a pocket opening toward the rear waist region is defined between these relatively large and small panels. Feces flowing from the rear waist region toward the crotch region is reliably received.

The feces retaining pocket of the diaper disclosed in Reference has a size when it is fully opened depending on a vertical dimension from f bottom of the depression to the smaller panel and a transverse dimension of the depression. To ensure that the pocket is adequately opened, the side of the pocket may be dimensioned as largely as desired. However, if a depth of the depression is increased in order to meet this requirement, a thickness of the larger panel will be correspondingly increased and the crotch region of the diaper will become correspondingly bulky. From another viewpoint, if the core of the smaller panel is swollen and/or a stiffness of this core is reduced as the smaller panel absorbs body fluid, the smaller panel may hang into the depression so as to reduce the opening size of the pocket and make it difficult for the pocket to receive feces reliably.

SUMMARY OF THE INVENTION

In view of the problem as has been described above, it is a principal object of this invention to provide the method for continuously making the disposable diaper including the feces retaining pocket formed by overlapping a pair of the panels each other, for example, as disclosed in Reference improved so that the size of the pocket when it is opened may be effectively enlarged by spacing a pair of panels from each other in a unique manner.

According to these first, second and third aspects, this invention provides a method for continuously making a disposable diaper, the disposable diaper defining a front waist region, a rear waist region and a crotch region extending between these two waist regions, the disposable diaper having a longitudinal direction, a transverse direction and a thickness direction and comprising a liquid-impervious sheet having a first inner surface and a first outer surface opposite to the first inner surface, a first body absorbent panel lying on the side of the first inner surface and having a second outer surface facing the first inner surface and a second inner surface opposite to the second outer surface, the first body fluid absorbent panel extending in the longitudinal direction over at least the rear waist region and the crotch region, and a second body fluid absorbent panel having a third outer surface facing at least a part of the second inner surface and a third inner surface opposite to the third outer surface, the second body fluid absorbent panel extending in the longitudinal direction over the front waist region and the crotch region but not to the rear waist region so that the second body fluid absorbent panel overlaps the first body fluid absorbent panel in the crotch region, wherein the second body fluid absorbent panel is bonded along its transversely opposite side edges to one of the liquid-impervious sheet and the first body fluid absorbent panel so that a region of the second body fluid absorbent panel defined between the transversely opposite side edges may be spaced from said first body fluid absorbent panel in the thickness direction, the method for continuously making the disposable diaper comprising that means to space the second body fluid absorbent panel from the first body fluid absorbent panel can be formed through a manufacturing process comprising steps as will be described below.

A method for continuously making a disposable diaper according to the first aspect of the invention comprises the steps of:

(1) continuously feeding first nonwoven fabric web destined to form the first body fluid absorbent panel in a first machine direction;

(2) placing first body fluid absorbent cores on an inner surface of the first nonwoven fabric web having the inner and outer surfaces intermittently in the first machine direction;

(3) continuously feeding a first liquid-pervious sheet in the first machine direction so that the first cores may be sandwiched between the first liquid-pervious sheet and the first nonwoven fabric web to form a first continuous assembly comprising a plurality of the first body fluid panels connected one with another in the first machine direction;

(4) continuously feeding second nonwoven fabric web destined to form the second body fluid absorbent panel in a second machine direction;

(5) placing second body fluid absorbent cores on inner surface of the second nonwoven fabric web having the inner surface and outer surface intermittently in the second machine direction;

(6) continuously feeding a second liquid-pervious sheet in the second machine direction so that the second cores may be sandwiched between the second liquid-pervious sheet and the second nonwoven fabric web to form a second continuous assembly comprising a plurality of the second body fluid panels connected one with another in the second machine direction;

(7) feeding the first and second continuous assemblies so as to flow into each other in a third machine direction which is an extension of the first and second machine directions so that the first liquid-pervious sheet and the second nonwoven fabric web may face each other, the first cores and second cores may fall in positions mutually aligned in the third machine direction and the first and second continuous assemblies may overlap each other in a cross direction crossing the third machine direction;

(8) bonding respective overlapping sections of the first and second continuous assemblies to each other in the vicinity of transversely opposite side edges of the second cores as viewed in the third machine direction to obtain a third continuous assembly consisting of the first and second continuous assemblies;

(9) successively cutting the third continuous assembly along cutting lines extending in the cross direction to obtain a plurality of first composites including each of the first cores as well as each of the second cores and first and second edges extending in parallel to each other defined by each pair of the cutting lines;

(10) continuously feeding a first liquid-impervious sheet having inner and outer surfaces in a fourth machine direction and placing the first composites one by one on the first liquid-impervious sheet with the first nonwoven fabric web sheet as well as the second nonwoven fabric web facing the inner surface of the first liquid-impervious sheet and then bonding respective peripheral edges of the first composites to the first liquid-impervious sheet to obtain a fourth continuous assembly;

(11) bonding a pair of continuous leak-barrier cuffs each having first and second side edges extending in parallel to each other, the second side edges made of belt-like material being elastically stretch- and contractable in a longitudinal direction thereof, along the first side edges to the fourth continuous assembly with the second side edges being stretched, in the vicinity of the first and second edges of the first composites attached to the fourth continuous assembly;

(12) placing the continuous cuffs bonded to the fourth continuous assembly in the vicinity of the first edge and the continuous cuffs bonded to the fourth continuous assembly in the vicinity of the second edge upon the first liquid-pervious sheet and the second liquid-pervious sheet with the second side edges facing to each other and then bonding the continuous cuffs to the first composites in the vicinity of respective ends crossing the first and second edges;

(13) partially bonding the second side edges of respective the continuous cuffs to the second liquid-pervious sheet in an intermediate region of the fourth continuous assembly as viewed in a cross direction crossing the fourth machine direction to form first one of the spacing means; and

(14) following said step (13), successively cutting the fourth continuous assembly along a line defined between each pair of adjacent the first composites to obtain individual the diapers or precursors of the individual diapers.

Of the diaper obtained by the method according to the first aspect of the invention, the first body fluid absorbent panel is formed by the first nonwoven fabric web and the first liquid-pervious sheet sandwiching the first core therebetween and the second body fluid absorbent panel is formed by the second nonwoven fabric web and the second liquid-pervious sheet sandwiching the second core therebetween. Each pair of the leak-barrier cuffs is formed by a pair of continuous cuffs. In response to contraction of the second side edges of the cuffs made of leak-barrier belt-like material as such diaper is put on the wearer's body, the second body fluid absorbent panel having the second liquid-pervious sheet bonded to the second side edges of the cuffs are lifted up to be spaced from the first body fluid absorbent panel. Consequentially, the first body fluid absorbent panel cooperates with the second body fluid absorbent panel to form the feces retaining pocket defining a large opening. The method according to the first aspect of the invention allows the leak-barrier cuffs to function as the first means to space the first and second body fluid absorbent panels from each other by bonding the continuous cuffs are to the second liquid-pervious sheet as has been described above.

According to one preferred embodiment of the invention on the first aspect, the first liquid-impervious sheet comprises liquid-impervious plastic film and a nonwoven fabric layer laminated on at least one of inner and outer surfaces of the film. The diaper made in this manner advantageously provides the wearer with comfortable cloth-like touch.

According to another preferred embodiment of the invention on the first aspect, the belt-like material comprises a nonwoven fabric layer and rubber thread attached in stretched state to the nonwoven fabric layer. The method of this manner facilitates the elastically stretch- and contractable leak-barrier cuffs to be made.

According to still another preferred embodiment of the invention on the first aspect, the first machine direction and the second machine direction coincide with a transverse direction of the liquid-impervious sheet while the fourth machine direction coincides with the longitudinal direction of the liquid-impervious sheet and the first composite is placed upon the first liquid-impervious sheet after the first composite has been turned by an angle of 90°. The method of this manner facilitates the elastic members continuously extending in the transverse direction to be attached to the diaper because the transverse direction of the diaper coincides with the first and second machine directions.

According to further another preferred embodiment of the invention on the first aspect, the step (6) is followed by the step (7) in which the second continuous assembly placed upon the first continuous assembly is partially folded back along folding guide lines extending in parallel to the second machine direction so that the second liquid-pervious sheet may overlap itself and the second nonwoven fabric web constituting the second continuous assembly may face the continuous cuffs and, in the step (13), the second side edges of said continuous cuffs are partially bonded to the second nonwoven fabric web instead of the second liquid-pervious sheet. The method of this manner allows the continuous cuffs to be bonded to the second nonwoven fabric web cooperating with the second liquid-pervious sheet to sandwich the second cores.

According to an additional preferred embodiment of the invention on the first aspect, the first machine direction and the second machine direction coincide with the longitudinal direction of the liquid-impervious sheet. With the method of this manner, it is possible to arrange the courses along which the first and second nonwoven fabric webs are fed above and below and thereby to reduce the transverse space in the production line because the longitudinal direction of the diaper coincides with both the first machine direction and the second machine direction.

According to further additional preferred embodiment of the invention on the first aspect, the first machine direction coincides with the longitudinal direction of the liquid-impervious sheet while the second machine direction coincides with the transverse direction of the liquid-impervious sheet and the method further include a step of turning the first body fluid absorbent panel obtained by cutting the first continuous assembly or the second body fluid absorbent panel obtained by cutting the second continuous assembly by an angle of 90°. The method of this manner facilitates the elastic members extending in the transverse direction of the diaper to be continuously fed and attached to the second nonwoven fabric web.

According to an alternative preferred embodiment of the invention on the first aspect, the method further includes a step of attaching, in stretched state, continuous spacer made of belt-like elastic material as second one of the spacing means functioning to reduce a width of the diaper in the crotch region thereby to space the first and second body fluid absorbent panels from each other to the first or second continuous assembly. The method of this manner allows the continuous cuffs as well as the continuous spacer as the means serving to reduce the width of the diaper.

A method for continuously making a disposable diaper according to the second aspect of the invention comprises the steps of:

(1) continuously feeding first nonwoven fabric web destined to form the first body fluid absorbent panel in a first machine direction;

(2) placing first body fluid absorbent cores on an inner surface of the first nonwoven fabric web having the inner and outer surfaces intermittently in the first machine direction;

(3) continuously feeding a first liquid-pervious sheet in the first machine direction so that the first cores may be sandwiched between the first liquid-pervious sheet and the first nonwoven fabric web to form a first continuous assembly comprising a plurality of the first body fluid panels connected one with another in the first machine direction;

(4) continuously feeding second nonwoven fabric web destined to form the second body fluid absorbent panel in a second machine direction;

(5) placing second body fluid absorbent cores on inner surface of the second nonwoven fabric web having the inner surface and outer surface intermittently in the second machine direction;

(6) continuously feeding a second liquid-pervious sheet in the second machine direction so that the second cores may be sandwiched between the second liquid-pervious sheet and the second nonwoven fabric web to form a second continuous assembly comprising a plurality of the second body fluid panels connected one with another in the second machine direction;

(7) feeding continuous spacer made of belt-like elastic material, in stretched state, in the first machine direction or in the second machine direction so that the continuous spacer may straddle the first cores in the first continuous assembly or the second cores in the second continuous assembly and bonding the continuous spacer to the first liquid-pervious sheet in the first continuous assembly or the second nonwoven fabric web in the second continuous assembly (8) feeing the first and second continuous assemblies so as to flow into each other in a third machine direction which is an extension of the first and second machine directions so that the first liquid-pervious sheet and the second nonwoven fabric web may face each other, the first cores and second cores may fall in the corresponding positions in the third machine direction and the first and second continuous assemblies may overlap each other in a cross direction crossing the third machine direction;

(9) bonding respective overlapping sections of the first and second continuous assemblies to each other in the vicinity of transversely opposite side edges of the second cores as viewed in the third machine direction to obtain a third continuous assembly consisting of the first and second continuous assemblies;

(10) successively cutting the third continuous assembly along cutting lines extending in the cross direction to obtain a plurality of first composites including each of the first cores as well as each of the second cores and first and second edges extending in parallel to each other defined by each pair of the cutting lines;

(11) continuously feeding a first liquid-impervious sheet having inner and outer surfaces in a fourth machine direction and placing the first composites one by one on the first liquid-impervious sheet with the first nonwoven fabric web sheet as well as the second nonwoven fabric web facing the inner surface of the first liquid-impervious sheet and then bonding respective peripheral edges of the first composites to the first liquid-impervious sheet to obtain a fourth continuous assembly; and

(12) following said step (11), successively cutting the fourth continuous assembly along a line defined between each pair of the adjacent first composites to obtain individual the diapers or precursors of the individual diapers.

According to the second aspect of this invention, the second spacing means to space the first and second body fluid absorbent panels from each other can be obtained by the step of bonding the continuous spacer made of belt-like elastic material, in stretched state, to the first continuous assembly or to the second continuous assembly so as to straddle the first cores or the second cores.

According to one preferred embodiment of the invention on the second aspect, the first liquid-impervious sheet comprises liquid-impervious plastic film and a nonwoven fabric layer laminated on at least one of inner and outer surfaces of the film. The diaper made in this manner advantageously provides the diaper wearer with comfortable cloth-like touch.

According to another preferred embodiment of the invention on the second aspect, the first machine direction and the second machine direction coincide with a transverse direction of the liquid-impervious sheet while the fourth machine direction coincides with the longitudinal direction of the liquid-impervious sheet and the first composite is placed upon the first liquid-impervious sheet after the first composite has been turned by an angle of 90°. The method of this manner facilitates the elastic members continuously extending in the transverse direction to be attached to the diaper because the transverse direction of the diaper coincides with the first and second machine directions.

According to still another preferred embodiment of the invention on the second aspect, the first machine direction and the second machine direction coincide with the longitudinal direction of the liquid-impervious sheet. With the method of this manner, it is possible to arrange the courses along which the first and second nonwoven fabric webs are fed above and below and thereby to reduce the transverse space in the production line because the longitudinal direction of the diaper coincides with both the first machine direction and the second machine direction.

According to further another preferred embodiment of the invention on the second aspect, the first machine direction coincides with the longitudinal direction of the liquid-impervious sheet while the second machine direction coincides with the transverse direction of the liquid-impervious sheet and the method further include a step of turning the first body fluid absorbent panel obtained by cutting the first continuous assembly or the second body fluid absorbent panel obtained by cutting the second continuous assembly by an angle of 90°. The method of this manner facilitates the elastic members extending in the transverse direction of the diaper to be continuously fed and attached to the second nonwoven fabric web.

According to an additional preferred embodiment of the invention on the second aspect, the method further includes a step of bonding a pair of continuous leak-barrier cuffs each having first and second side edges extending in parallel to each other, the second side edges made of belt-like material being elastically stretch- and contractible in a longitudinal direction thereof, along the first side edges to the fourth continuous assembly with the second side edges being stretched, in the vicinity of the first and second edges of the first composites attached to the fourth continuous assembly. With the method of this manner, the continuous cuffs can be linearly fed in the fourth machine direction and attached to the fourth continuous assembly running in the fourth machine direction.

According to further additional preferred embodiment of the invention on the second aspect, the method further includes a step of partially bonding the continuous cuffs to any one of the second liquid-pervious sheet and the second nonwoven fabric web sandwiching the second cores. The method of this manner allows the leak-barrier cuffs to function as the additional means to space the first and second body fluid absorbent panels of the diaper from each other.

A method for continuously making a disposable diaper according to the invention on the third aspect comprises the steps of:

(1) continuously feeding said liquid-impervious sheet having said first inner surface and said first outer surface in a first machine direction;
(2) attaching said first body fluid absorbent panels to said first inner surface of said continuously fed liquid-impervious sheet so that each of said first body fluid absorbent panels may extend at least over a section allocated for said rear waist and crotch regions;
(3) placing said second body fluid absorbent panels on said continuously fed liquid-impervious sheet so that each of said second body fluid absorbent panels may extend over a section of said continuously fed liquid-impervious sheet allocated for said front waist and crotch regions and said second outer surface of said second body fluid absorbent panel may face said first inner surface of said first body fluid absorbent panel in said crotch region and then bonding, in said crotch region, said transversely opposite edges of said second body fluid absorbent panel to transversely opposite side edges of said first body fluid absorbent panel or to transversely opposite side edges of said continuously fed liquid-impervious sheet extending outside said transversely opposite side edges of said first body fluid absorbent panel;
(4) feeding, in stretched state, a pair of leak-barrier cuff members formed by belt-like material extending from said section allocated for said crotch region to said sections allocated for said front and rear waist regions, said belt-like material being elastically stretch- and contractable in a direction in which said belt-like material extends and having inner and outer side edges, to said continuously fed liquid-impervious sheet having said first and second body fluid absorbent panels attached thereto, then, in said crotch regions, attaching said outer side edges of said respective cuff members to said continuously fed liquid-impervious sheet outside respective said side edges of said first and second body fluid absorbent panels and covering edges of said first and second body fluid absorbent panels with said inner side edges of respective said cuff members; and
(5) forming said spacing means by at least one of substeps a) and b) as follow:
 a. bonding, in each section of said continuously fed liquid-impervious sheet allocated for said crotch region, portions of said inner side edges of said leak-barrier cuff members in stretched state to the portions of said second body fluid absorbent panel covered with said portions of said inner side edges; and
 b. attaching, in each section of said continuously fed liquid-impervious sheet allocated for said crotch region, a belt-like elastic spacer transversely extending in stretched state between said first and second body fluid absorbent panels to said side edges of at least one of said first and second body fluid absorbent panels.

In such manufacturing process according to the third aspect of the invention, the first and/or second means to space the second body fluid absorbent panel from the first body fluid absorbent panel can be obtained by at least one of substeps of bonding, in each section of the continuously fed liquid-impervious sheet allocated for the crotch region, portions of the inner side edges of the leak-barrier cuff members in stretched state to the portions of the second body fluid absorbent panel covered with the portions of the inner side edges; and attaching, in each section of the continuously fed liquid-impervious sheet allocated for the crotch region, a belt-like elastic spacer transversely extending in stretched state between the first and second body fluid absorbent panels to the side edges of at least one of the first and second body fluid absorbent panels.

DETAILED DESCRIPTION OF THE PREFERRED EMBODIMENTS

Details of a method according to this invention for continuously making the disposable diaper will be more fully understood from the description given hereunder with reference to the accompanying drawings.

Figure 1:
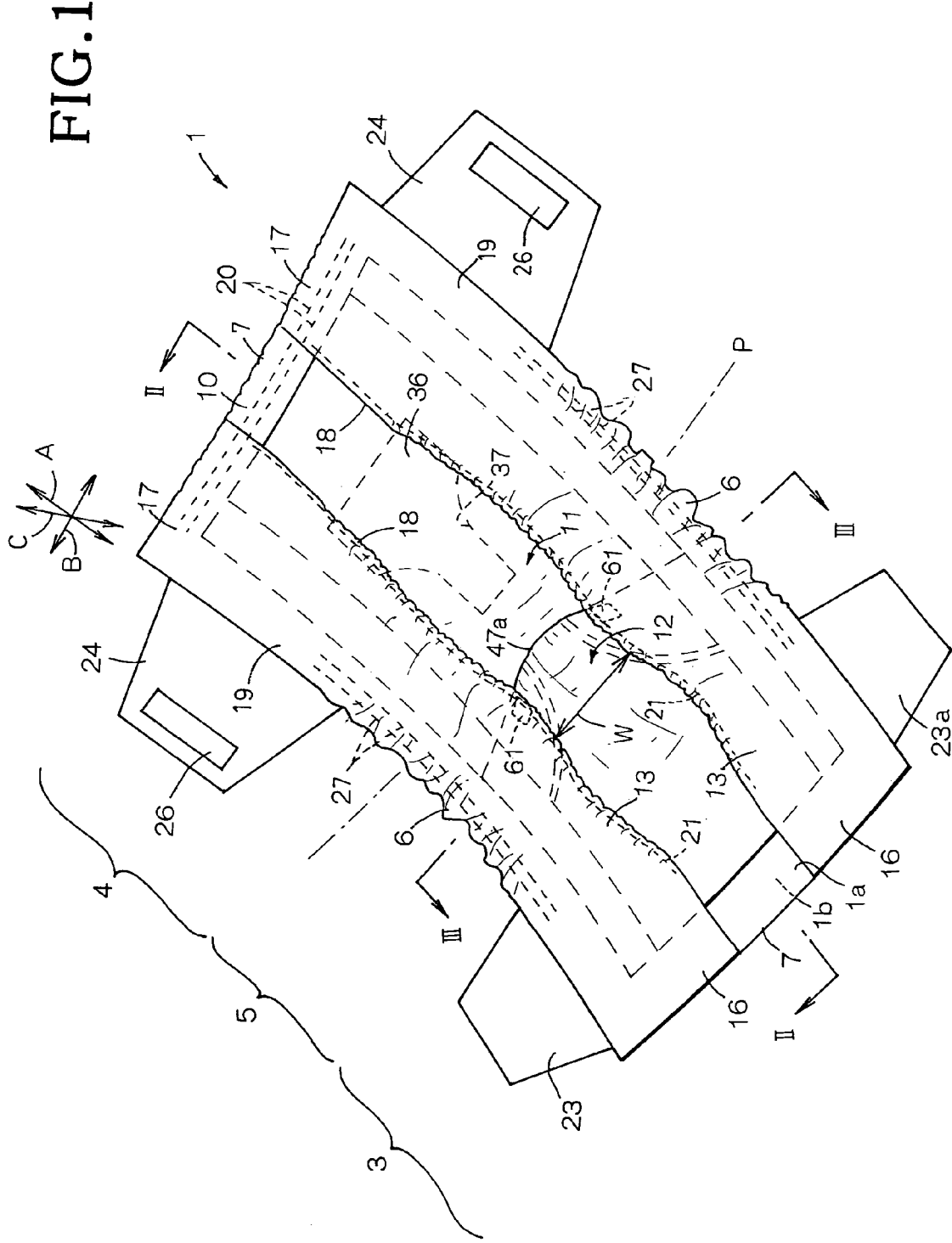
FIG. 1 is a perspective view showing a diaper obtained by the process according to the invention.

FIG. 1 is a perspective view showing a disposable diaper 1 obtained by the inventive method. The diaper 1 has an inner surface 1a facing the diaper wearer's skin and an outer surface 1b facing away from the wearer's skin. The diaper 1 has a longitudinal direction, a transverse direction and a thickness direction being orthogonal one to another as indicated by double-headed arrows A, B and C, respectively. The longitudinal direction A can be referred to also as the back-and-forth direction of the diaper 1 and the transverse direction can be referred to also as the width direction of the diaper 1. In this diaper 1, a rectangular panel-like component 2 which is relatively long in the longitudinal direction A comprises a front waist region 3, a rear waist region 4 and a crotch region 5 extending between these two waist regions 3, 4 and is contoured by a pair of transversely opposite side edges 6 extending in parallel to each other in the longitudinal direction A and a pair of longitudinally opposite ends extending in parallel to each other in the transverse direction B. The panel-like component 2 further comprises a liquid-impervious liner sheet 10 which is, in turn, provided on its inner surface with first and second body fluid absorbent panels 11, 12. These panels 11, 12 are partially covered with a pair of leak-barrier cuffs 13, respectively, extending in the longitudinal direction A long the respective side edges 6 of the panel-like component 2. Each of these leak-barrier cuffs 13 has a front end 16, a rear end 17, an inner side edge 18 and an outer side edge 19 wherein the front and rear ends 16, 17 as well as the outer side edge 19 are bonded to the liner sheet 10. An elastic member 21 is attached in stretched state to the inner side edge 18. The panel-like component 2 is further provided in the rear waist region 4 with a waist elastic member 20 attached in stretched state thereto and provided in the vicinity of the respective side edges 6 with leg elastic members 27 attached in stretched state thereto. It should be noted that FIG. 1 shows the panel-like component 2 bowing in the longitudinal direction A with the outer surface 1b of the diaper 1 being convex as the elastic members 20, 21, 27 contract. In such panel-like component 2, the front waist region 3 has a pair of front wings 23 extending in the transverse direction B and the rear waist region 4 has a pair of rear wings 24 extending in the transverse direction B. The rear wings 24 are respectively provided on the inner surfaces thereof with fasteners 26 adapted to be detachably anchored on the outer surface of the front waist region 3 or the outer surfaces of the respective front wings 23 at predetermined positions thereon.

Figure 2:
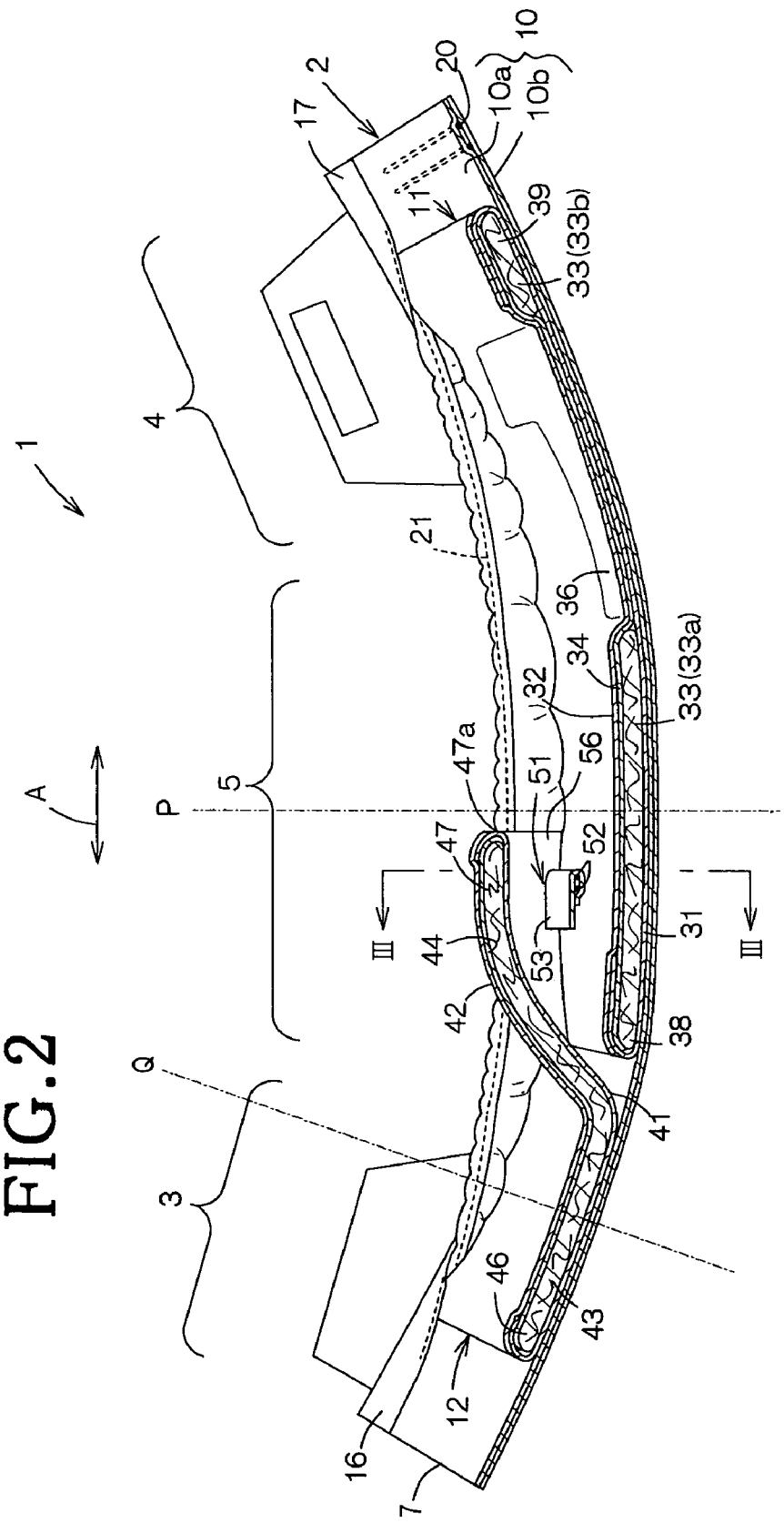
FIG. 2 is a sectional view taken along the line II—II in FIG. 1.

FIG. 2 is a sectional view taken along the line II—II in FIG. 1, showing the diaper 1 which is bowing in the longitudinal direction. In the panel-like component 2, the liner sheet 10 comprises an inner sheet 10a made of liquid-impervious plastic film and an outer sheet 10b laminated with each other and the waist elastic member 20 is interposed between these two sheets 10a, 10b and bonded to at least one of these two sheets. The first panel 11 extends at least over the rear waist region 3 and the crotch region 5 of the panel-like component 2. In the case of the illustrated embodiment, the first panel 11 has a front section 38 placed aside toward the front waist region 3 and a rear section 39 placed aside toward the rear waist region 4. Such first panel 11 comprises a first outer sheet 31 made of nonwoven fabric, preferably liquid-impervious nonwoven fabric, a first inner sheet 32 made of liquid-pervious nonwoven fabric and a first body fluid absorbent core 33 interposed between these two sheets 31, 32. The first core 33 is a mixture of fluff pulp and body fluid absorbent material such as super-absorbent polymer particles. Preferably, surfaces of such mixture destined to come in contact with the first outer sheet 31 and the first inner sheet 32, respectively, or at least the surface destined to come in contact with the first inner sheet 32 are or is covered with a liquid-pervious first body fluid spreadable sheet 34 such as tissue paper. It should be noted that the first core 33 in the illustrated embodiment is divided into a front section 33a and a rear section 33b between which the first inner sheet 32 and the first body fluid spreadable sheet 34 bow so as to be placed upon the first outer sheet 31 and to form the first panel 11 with a depression 36. In FIG. 1, this depression 36 is indicated by chain lines 37 describing a substantially T-shape.

The second panel 12 of the panel-like component 2 comprises a second outer sheet 41 made of nonwoven fabric, preferably of liquid-pervious nonwoven fabric, a second inner sheet 42 made of liquid-pervious nonwoven fabric and a second body fluid absorbent core 43 interposed between these two sheets 41, 42. The second core 43 is a mixture of fluff pulp and body fluid absorbent material such as super-absorbent polymer particles. Preferably, surfaces of such mixture destined to come in contact with the second outer sheet 41 and the second inner sheet 42, respectively, or at least the surface destined to come in contact with the second inner sheet 42 are or is covered with a liquid-pervious second body fluid spreadable sheet 44 such as tissue paper. Such second panel 12 extends over the front waist region 3 and a part of the crotch region 5 but not to the rear waist region 4. Thus the second panel 12 has a front section 46 lying in the front waist region 3 and a rear section 47 lying in the crotch region 5. The front section 46 is bonded to the liner sheet 10 by means of adhesive (not shown). The rear section 47 is formed so as to be separably placed upon the first panel 11 in the crotch region 5. In FIG. 2, this rear section 47 is lifted up and thereby spaced from the first panel 11. In a preferred diaper 1, a rear end 47a (See FIG. 1 also) of the rear section 47 lies between a centerline P bisecting a dimension of the diaper 1 in the longitudinal direction A and a line Q bisecting a dimension from the centerline P to the front end 7 of the panel-like component 2. Between the front section 38 of the first panel 11 and the rear section 47 of the second panel 12 spaced from each other, a belt-like spacer 51 is interposed. The spacer 51 comprises at least a single rubber thread covered, in stretched state, with nonwoven fabric 53. Such spacer 51 is stretched in the transverse direction B of the diaper 1 and attached to the diaper 1 in such stretched state. FIG. 2 shows the rubber thread 52 let free to contract.

In the crotch region 5 of such diaper 1, the rear section 47 of the second panel 12 define a wall dividing the diaper 1 in front and rear halves and cooperates with the front section 38 of the first panel 38 to define a pocket 56 opening toward the rear waist region 5.

Figure 3:
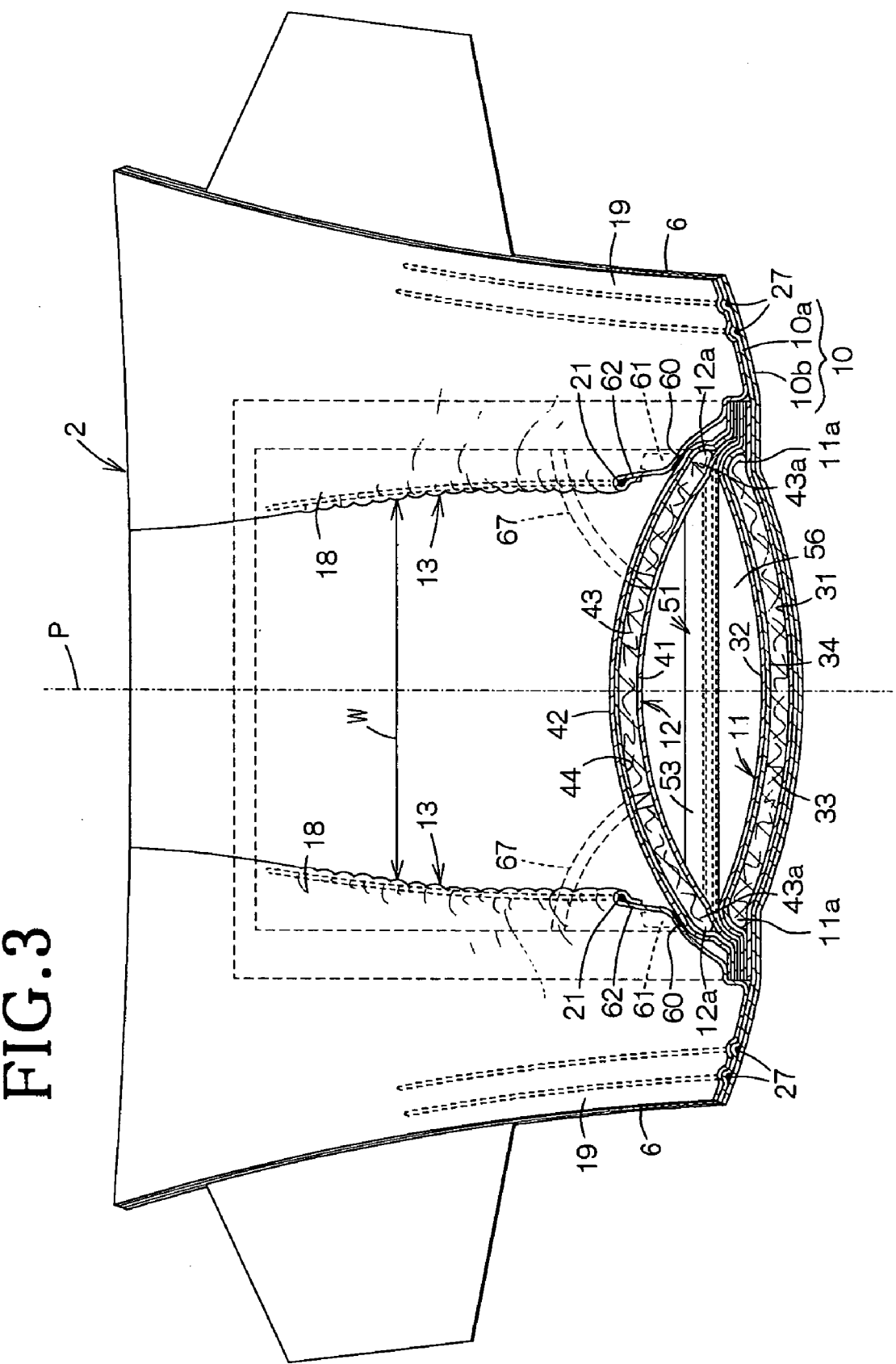
FIG. 3 is a sectional view taken along the line III—III in FIG. 1.

FIG. 3 is a sectional view taken along the line III—III in FIG. 2. The line III—III lies aside from the centerline P toward the front waist region 3 and extends through the first panel 11 and the second panel 12. In the vicinity of the respective side edges 6 of the panel-like component 2, the leg elastic members 27 are interposed between the outer sheet 10a and the inner sheet 10b and bonded to at least one of these sheets 10a, 10b. Along the respective side edges 11a of the first panel 11, the first outer sheet 31, the first inner sheet 32 and the first body fluid spreadable sheet 34 extend sideways beyond the first core 33 and bonded together and bonded also to the inner sheet 10b by means of adhesive or any suitable welding technique. Along the side edges 12a of the second panel 12, the second outer sheet 41, the second inner sheet 42 and the second body fluid spreadable sheet 44 extend sideways beyond the second core 43 and bonded together and bonded also to the first inner sheet 32 of the first panel 11 by means of adhesive or any suitable welding technique. The spacer 51 extends between the side edges 11a, 11a of the first panel 11 as well as between the side edges 12a, 12a of the second panel 12, straddling the first and second cores 33, 43. In the vicinity of the side edges 43a of the core 43, the spacer 51 is bonded to the first inner sheet 32 and/or the second outer sheet 41 by means of adhesive or any suitable welding technique. The leak-barrier cuffs 13 respectively have the outer side edges 19 lying outside the side edges 11a of the first panel 11 as well as the side edges 12a of the second panel 12 and bonded to the inner sheet 10a by means of adhesive or any suitable welding technique. The inner side edges 18 of the respective leak-barrier cuffs 13 partially cover the first panel 11 and the second panel 12 (See FIG. 1). These inner side edges 18 are bonded to the second inner sheet 42 of the second panel 12 by means of adhesive 60 along regions 61 indicated by chain lines in the vicinity of the respective elastic members 21. Regions 62 defined between the elastic members 21 and the aforementioned regions 61 rise above the second inner sheet 42 as the elastic members 21 contract. Between a pair of the leak-barrier cuffs 13 constructed in this manner, the inner side edges 18 are spaced from each other by a dimension W so that the first panel 11 as well as the second panel 12 are partially exposed between these inner side edges 18 (See FIG. 1). In the case of the diaper 1 for baby or infant, the dimension W is preferably in a range of about 20 to about 50 mm.

Figure 4:
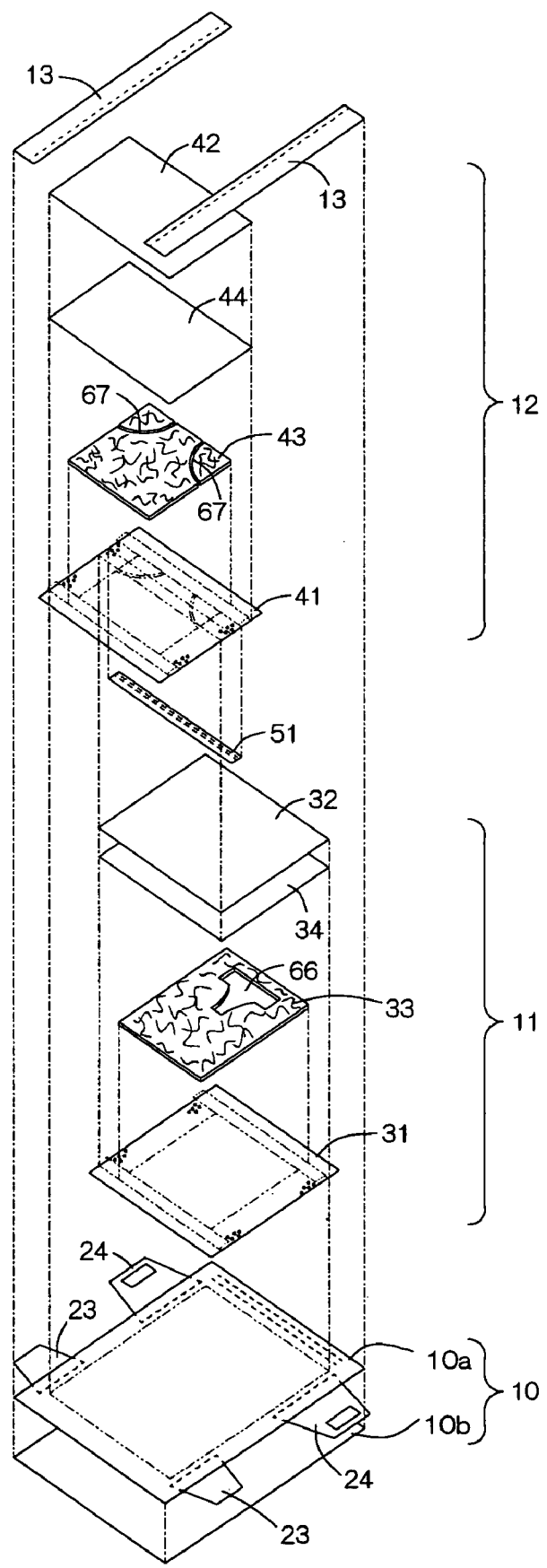
FIG. 4 is an exploded perspective view showing the diaper.

FIG. 4 is an exploded perspective view of the diaper 1. At the bottom of FIG. 4, the inner sheet 10a and the outer sheet 10b are shown as before laminated to form the liner sheet 10. The inner sheet 10a is provided with a pair of the front wings 23 and a pair of the rear wings 24 attached thereto. Above the inner sheet 10a, the first outer sheet 31, the first core 33, the first body fluid spreadable sheet 34 and the first inner sheet 32 forming together the first panel 11 are shown in this order from the bottom. Above the first inner sheet 32, the spacer 51 is shown. Above the spacer 51, the second outer sheet 41, the second core 43, the second body fluid spreadable sheet 44 and the second inner sheet 42 forming together the second panel 12 are shown in this order from the bottom. Above the second inner sheet 42, a pair of the leak-barrier cuffs 13 is shown. Referring to FIG. 4, imaginary lines extending in the first outer sheet 31 and the second outer sheet 41 indicate guiding lines along which these sheets 31, 41 are folded in the course of the method for making the diaper 1. A region 66 in the first core 33 is devoid of core material and this region 66 is destined to form the depression 33 as shown by FIG. 2. A pair of arc-shaped regions 67 in the second core 43 are also devoid of core material and facilitate the second panel 12 to be deformed around the wearer's legs as the diaper 1 is put on the wearer's body. Such regions 67 appear in FIG. 3 also.

The diaper 1 constructed in the manner as has been described above bows in the longitudinal direction A as it is put on the wearer's body whereupon the inner side edges 18 of the respective leak-barrier cuffs 13 rise toward the inner side of the diaper 1 (upward as viewed in FIG. 1), i.e., move in a direction from the outer surface toward the inner surface of the liner sheet 10 as the elastic members 21 contract. Thereupon, the second panel 12 bonded to the leak-barrier cuffs 13 along the regions 61 is deformed to be lifted off from the first panel 11 and thereby to broaden the opening of the pocket 56. In this invention, the leak-barrier cuffs 13 functioning in this manner can serve as first important means to space the first and second panels 11, 12 from each other. As exemplarily shown by FIG. 3, the first panel 11 is deformed to become convex toward the outer side of the diaper 1 (i.e., downward as viewed in FIG. 1) while the second panel 12 is deformed to become convex toward the inner side of the diaper 1 as the spacer 51 elastically contracts in the transverse direction B of the diaper 1. In this way, the pocket 56 is opened more significantly than the diaper 1 having not the spacer 51. The spacer 51 functioning in this manner can serve as second important means to space the first and second panels 11, 12 from each other. The rear section 47 of the second panel 12 deformed to become convex toward the inner side of the diaper 1 has its rear end 47a lies between the lines P and Q, in other words, between the genital organ and the anus of the diaper wearer. Such rear section 47 functions, for example, to block loose passage flowing from the rear waist region 4 or the crotch region 5 toward the front waist region 3 and to guide this into the pocket 56 and/or to block urine flowing from the front waist region 3 or the crotch region 5 toward the rear waist region 4. In this way, the rear section 47 is able to avoid the apprehension that loose passage and urine might be mixed with each other in the crotch region 5 and the wearer's skin might be contaminated with this mixture.

It should be understood that, in the diaper 1, the second panel 12 can be effectively spaced from the first panel 11 merely by adopting one of two means as have been described above, i.e., bonding the leak-barrier cuffs to the second panel 12 along the regions 61 and provision of the spacer 51. Which means should be adopted depends on various factors such as the contractile forces of the elastic members 21 and the elastic member(s) 52 and the flexural stiffness of the first and second panels 11, 12 in the transverse direction B. In the diaper 1, the inner surfaces of the first core 33 and the second core 43 may be covered with the body fluid spreadable first sheet 34 and the body fluid spreadable second sheet 44, respectively, to facilitate body fluid to spread on the respective inner surfaces of these cores 33, 43. In addition, if these cores 33, 43 contain superabsorbent polymer particles, the sheets 34, 44 are able to prevent falling off of such particles from the first and second cores 33, 43. The body fluid spreadable first and second sheets 34, 44 functioning as has been described above may cover, in addition to the inner surfaces of the first and second cores 33, 43, the outer surfaces thereof. If the first inner sheet 32 and the second inner sheet 42 have the same function as that of the first and second body fluid spreadable sheets 34, 44, these first and second body fluid spreadable sheets 34, 44 may be left out from the diaper 1. If it is unnecessary to form the first panel 11 of the diaper 1 with the depression 36, it is possible to use the first core 33 having not the region 66, instead of the first core 33 as seen in FIG. 4. The waist elastic member 20 as well as the leg elastic members 27 may be also left out if unnecessary.

Figure 5:
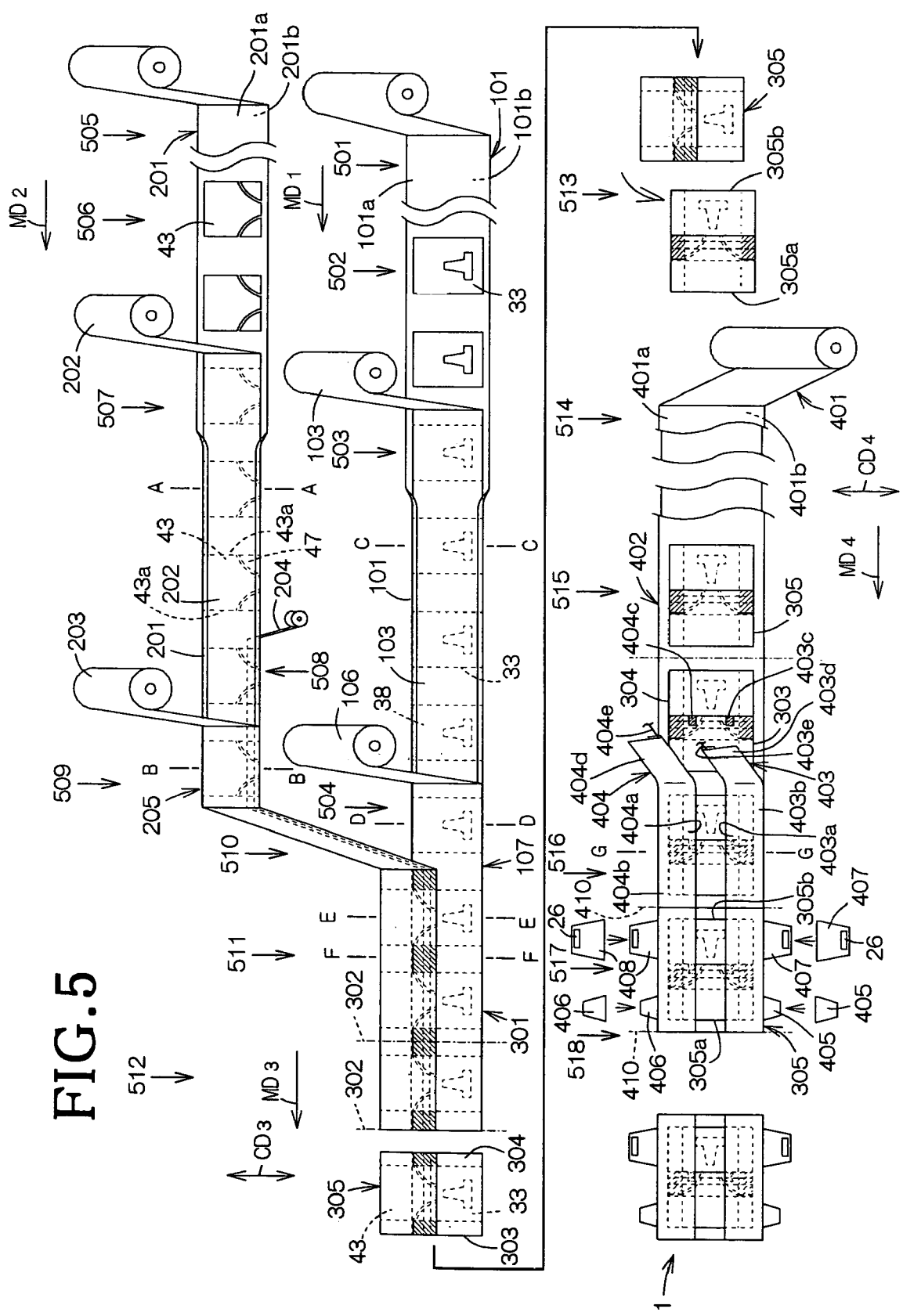
FIG. 5 is a diagram illustrating the process for making the diaper.

FIG. 5 is a diagram exemplarily illustrating the process for continuously making the diaper of FIG. 1. In a first step 501, first continuous nonwoven fabric web 101 is fed in a first machine direction $MD_1$. The first continuous nonwoven fabric web 101 has an inner surface 101a and an outer surface 101b. In a second step 502, the inner surface 101a is coated with hot melt adhesive (not shown), then the first cores 33 of FIG. 2 are arranged intermittently in the first machine direction $MD_1$ and these first cores 33 are coated on the inner surfaces thereof with hot melt adhesive (not shown). In a third step 503, a first continuous body fluid-pervious and -spreadable sheet 103 is fed in the first machine direction $MD_1$ so that the respective first cores 33 may be sandwiched between the first continuous body fluid spreadable sheet 103 and the first continuous nonwoven fabric web 101, then transversely opposite side edges of the first continuous nonwoven fabric web 101 are folded about and sealed with transversely opposite side edges of the first continuous body fluid spreadable sheet 103 by means of adhesive or any suitable welding technique. In a fourth step 504, a first continuous liquid-pervious sheet 106 which is body fluid-pervious is fed in the first machine direction $MD_1$ so that the first cores 33 and the first continuous body fluid spreadable sheet 103 may be sandwiched between the first continuous liquid-pervious sheet 106 and the first continuous nonwoven fabric web 101, then the first continuous liquid-pervious sheet 106 is bonded to the first continuous body fluid spreadable sheet 103 and the first continuous nonwoven fabric web 101 by means of adhesive or any suitable welding technique to obtain first continuous assembly 107.

In a fifth step 505, second continuous nonwoven fabric web 201 is fed in a second machine direction $MD_2$. The second continuous nonwoven fabric web 201 has an inner surface 201a and an outer surface 201b. In a sixth step 506, the inner surface 201a is coated with hot melt adhesive (not shown), then the second cores 43 of FIG. 2 are arranged intermittently in the second machine direction $MD_2$ and the second cores 43 are coated on the inner surfaces thereof with hot melt adhesive (not shown). In a seventh step 507, a second continuous body fluid spreadable sheet 202 such as tissue paper which is body fluid-pervious and -spreadable is fed in the second machine direction $MD_2$ so that the respective second cores 43 may be sandwiched between the second continuous body fluid spreadable sheet 202 and the second continuous nonwoven fabric web 201 while transversely opposite side edges of the second continuous nonwoven fabric web 201 are folded about and sealed with transversely opposite side edges of the second continuous body fluid spreadable sheet 202 by means of adhesive or any suitable welding technique. In a eighth step 508, elastically stretch- and contractable continuous spacer 204 is fed under tension onto the outer surface 201b of the second continuous nonwoven fabric web 201 in the second machine direction $MD_2$ so as to straddle the rear sections 47 of the respective second cores 43 (See FIG. 2) and then bonded to the second continuous nonwoven fabric web 201 in the vicinity of the side edges 43a of the respective second cores 43 (See FIG. 3) by means of adhesive or any suitable welding technique. In a ninth step 509, a second continuous liquid-pervious sheet 203 which is body fluid-pervious is fed in the second machine direction $MD_2$ so that the second cores 43 and the second continuous body fluid spreadable sheet 202 may be sandwiched between the second liquid-pervious sheet 203 and the second continuous nonwoven fabric web 201 while the second continuous liquid-pervious sheet 203 is bonded to the second continuous body fluid spreadable sheet 202 and the second continuous nonwoven fabric web 201 by means of adhesive or any suitable welding technique to obtain a second continuous assembly 205.

A third machine direction $MD_3$ is the direction in which the first continuous assembly 107 and the second continuous assembly 205 are fed together and this direction $MD_3$ is an extension of the first machine direction $MD_1$ and the second machine direction $MD_2$. In a tenth step 510 proceeding in this third machine direction $MD_3$, the first continuous assembly 107 and the second continuous assembly 205 are let flow into each other in a third cross direction $CD_3$ crossing the third machine direction $MD_3$ so that the first cores 33 and the second cores 43 may fall in the corresponding positions in the third machine direction $MD_3$ and the rear sections 47 of the second cores 43 may overlap the front sections 38 (See FIG. 2) of the first cores 33 from above. In an eleventh step 511, the first continuous liquid-pervious sheet 106 and the second continuous nonwoven fabric web 201 are bonded to each other by means of adhesive or any suitable welding technique in a shaded region defined between each pair of the adjacent second cores 43, 43 to obtain a third continuous assembly 301. In a twelfth step 512, the third continuous assembly 30 is successively cut along cutting lines 302 extending in the third cross direction $CD_3$ to obtain first composites 305 each comprising one of the first cores 33 and one of the second cores 43 and having first and second side edges 303, 304 defined by a pair of the adjacent cutting lines 302, 302. In a thirteenth step 513, the first composite 305 is turned by an angle of 90°. The first composite 305 having been turned in this manner has front and rear ends 305a, 305b.

In a fourteenth step 514 proceeding in a fourth machine direction $MD_4$, a continuous liquid-impervious sheet 401 having an inner surface 401a and an outer surface 401b is fed in this fourth machine direction $MD_4$. In the case of the continuous liquid-impervious sheet 401 exemplarily shown, the inner surface 401a is defined by liquid-impervious plastic film and the outer surface 401b is defined by nonwoven fabric wherein these film and nonwoven fabric are laminated together by means of adhesive or any suitable welding technique. In a fifteenth step 515, the first composites 305 having been turned by 90° in the thirteenth step 513 are placed upon the continuous liquid-impervious sheet 401 intermittently in the fourth machine direction $MD_4$ with the first and second continuous nonwoven fabric webs 101, 201 facing the inner surface 401a of the continuous liquid-impervious sheet 401 and then peripheral edges of the first composites 305 are bonded to the inner surface 401a by means of adhesive or any suitable welding technique to obtain a fourth continuous assembly 402. In a sixteenth step 516, first and second continuous cuffs 403, 404 which are elastically stretch- and contractable belt-like members for leak-barrier are respectively fed under tension in the fourth machine direction $MD_4$ and outer edges 403b, 404b of these first and second continuous cuffs 403, 404 are bonded to the fourth continuous assembly 402 by means of adhesive or any suitable welding technique in the vicinity of the first and second edges 303, 304, respectively, of the first composites 305. Also in a sixteenth step 516, the first and second continuous cuffs 403, 404 are placed upon the first continuous liquid-pervious sheet 106 and the second continuous liquid-pervious sheet 203 with inner edges 403a, 404a of the first and second continuous cuffs 403, 404 being opposed to each other and then the first and second continuous cuffs 403, 404 are bonded to the fourth continuous assembly 402 in the vicinity of the front and rear edges 305a, 305b of the first composites 305. In the same step 516, the inner edges 403a, 404a of the first and second continuous cuffs 403, 404 are partially bonded, in an intermediate region of the fourth continuous assembly 402 in a fourth cross direction $CD_4$ crossing the fourth machine direction $MD_4$, to the second continuous liquid-pervious sheet 203 by means of adhesives 403c, 404c. The first and second continuous cuffs 403, 404 fed in the sixteenth step 516 respectively comprise nonwoven fabric webs 403d, 404d which are continuous in the fourth machine direction $MD_4$ and rubber threads 403e, 404e attached in stretched state to these nonwoven fabric webs 403d, 404d. In a seventeenth step 517, respective edges of the fourth continuous assembly 402 are provided at predetermined positions with wing members 405, 406, 407, 408 destined to form the front wings 23 and the rear wings 24, respectively. The wing members 407, 408 are provided with the fasteners 26 of FIG. 1 attached thereto. In a eighteenth step 518, the fourth continuous assembly 402 is successively cut, between a pair of the adjacent first composites 305, along cutting lines 410 extending in the fourth cross direction $CD_4$ to obtain the individual diapers 1 or precursors of these diapers 1 between a pair of the adjacent first composites 305. As used herein a term "precursor" refers to the diaper destined to be subjected to any subsequent working.

The diaper obtained through the manufacturing process as has been described above is similar to the diaper 1 of FIG. 1 except that this diaper is provided with neither the waist elastic member nor the leg elastic members. These elastic members will be described in details with reference to FIGS. 6 and 7. In the diaper 1 obtained through the manufacturing process illustrated by FIG. 5, the step of feeding the continuous spacer 204 in the eighth step 508 may be left out if the spacer 51 is unnecessary for the diaper 1 of FIGS. 2 and 3. If it is unnecessary for the diaper 1 to use the leak-barrier cuffs 13 as the means to space the second panel 12 from the first panel 11, the step of partially bonding the inner edges 403a, 404a of the first and second continuous cuffs 403, 404 to the second continuous liquid-pervious sheet 203 by means of adhesive 403c, 404c may be left out. Furthermore, if the first body fluid spreadable sheet 34 and the second body fluid spreadable sheet 44 are unnecessary for the diaper 1, feeding of the first continuous body fluid spreadable sheet 103 in the third step 503 and feeding of the second continuous body fluid spreadable sheet 202 in the seventh step 507 may be left out. As will be apparent from comparison between the diaper 1 of FIG. 1 and the manufacturing process of FIG. 5, the first panel 11 is obtained from the first continuous nonwoven fabric web 101, the first core 33, the first continuous body fluid spreadable sheet 103 and the first continuous liquid-pervious sheet 106 illustrated in FIG. 5 while the second panel 12 is obtained from the second continuous nonwoven fabric web 201, the second core 43, the second continuous body fluid spreadable sheet 202, the continuous spacer 204 and the second continuous liquid-pervious sheet 203.

Figure 6:
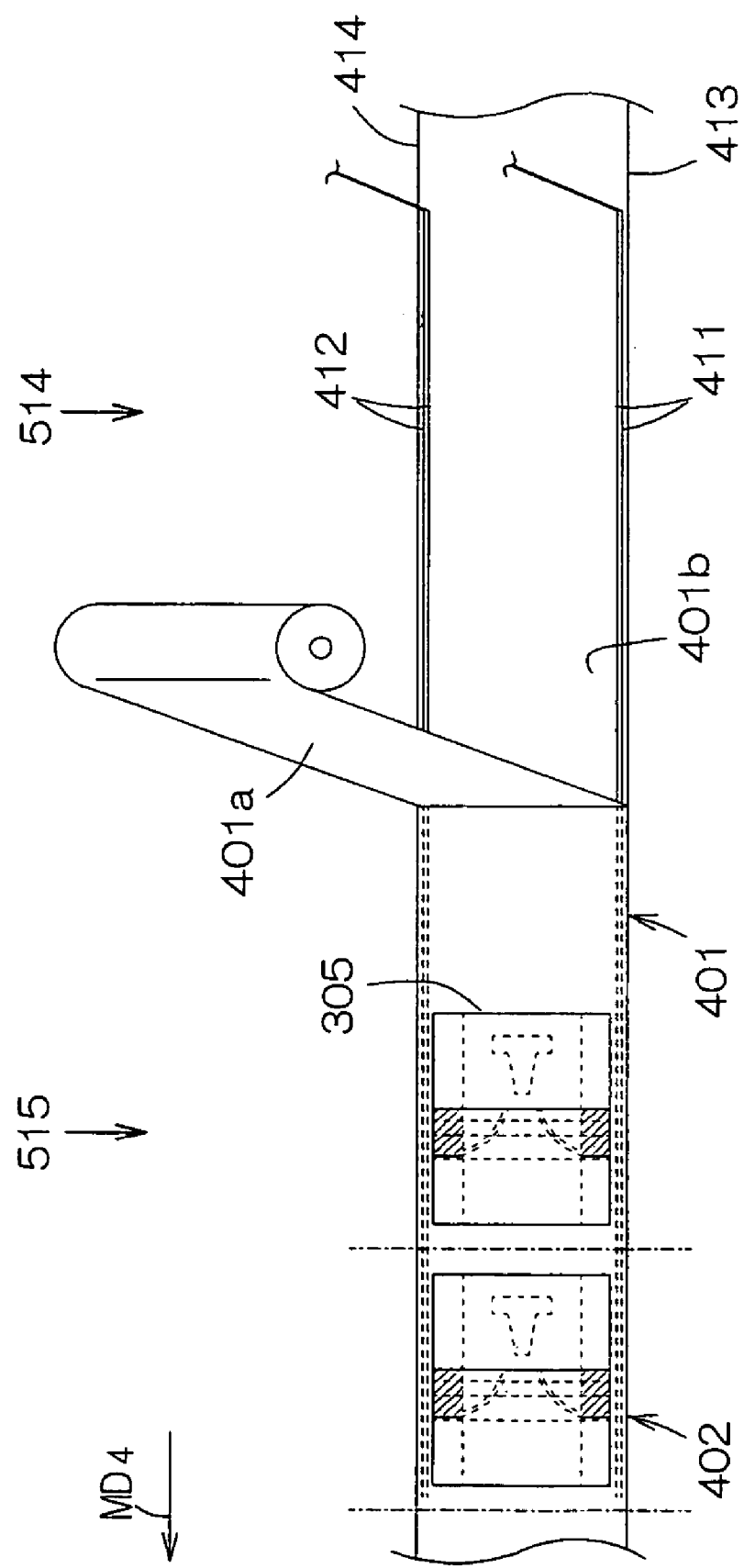
FIG. 6 is a diagram partially illustrating the process according to one preferred embodiment of the invention.

FIG. 6 illustrates the fourteenth step 514 and the fifteenth step 515 which are different from those in FIG. 5. In the fourteenth step 514 illustrated by FIG. 6, continuous elastic members 411, 412 destined to form the leg elastic members 27 in FIG. 1 are attached in stretched state to the outer sheet 401b constituting the continuous liquid-impervious sheet 401 along the side edges 413, 414 thereof by means of adhesive (not shown). Then the inner sheet 401a and the outer sheet 401b are bonded together by means of adhesive (not shown) to obtain the continuous liquid-impervious sheet 401. In the step 515, the first composites 305 are bonded to the continuous liquid-impervious sheet 401 to obtain the fourth continuous assembly 402. This fourth continuous assembly 402 may be utilized to attach the leg elastic members to the diaper 1 obtained through the manufacturing process illustrated by FIG. 5.

Figure 7:
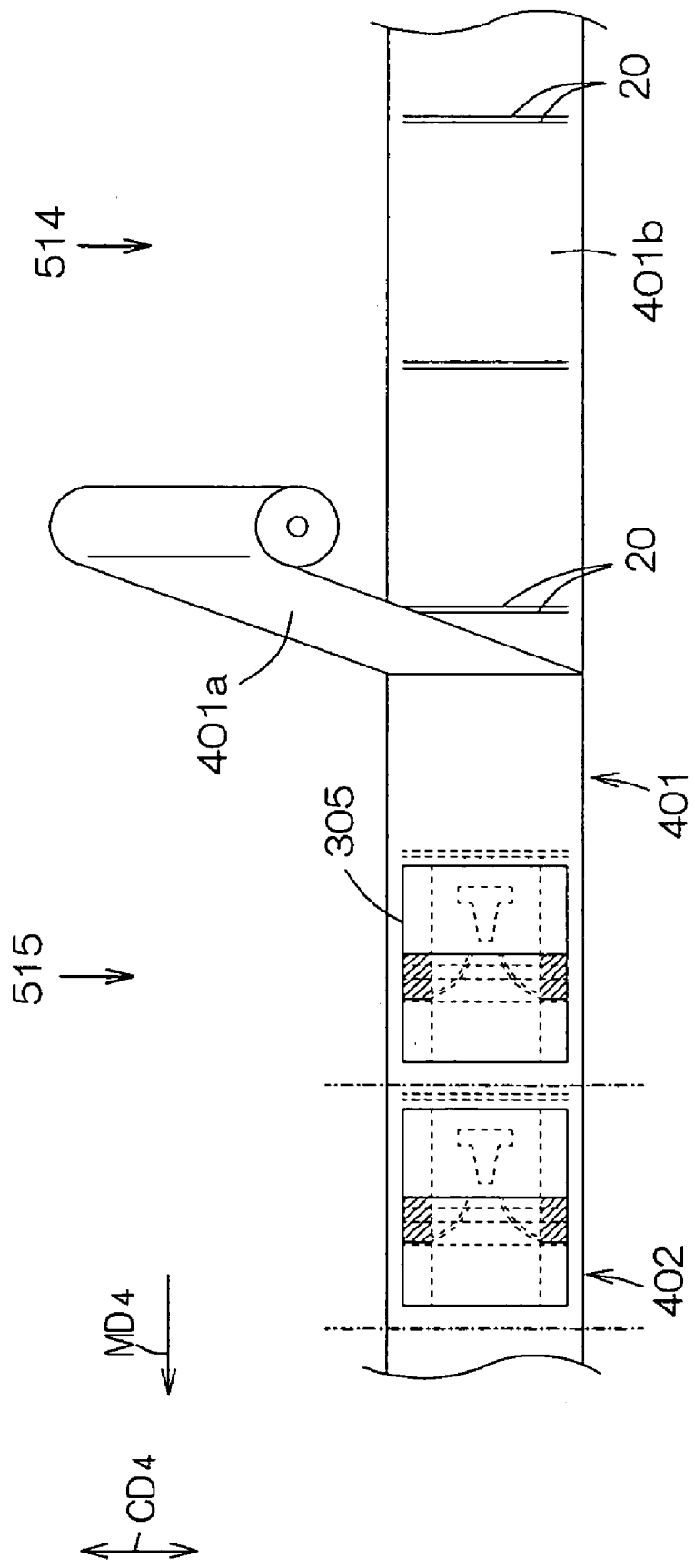
FIG. 7 is a diagram partially illustrating the process according to another preferred embodiment of the invention.

FIG. 7 also illustrates the fourteenth step 514 and the fifteenth step 515 which are different from those in FIG. 5. In the fourteenth step 514 of FIG. 7, the elastic members 20 (See FIG. 1) each extending in the fourth cross direction $CD_4$ are bonded in stretched state to the outer sheet 401b constituting the continuous liquid-impervious sheet 401 by means of adhesive (not shown). Each of the elastic members 20 corresponds to the waist elastic member 20 of the diaper 1 shown by FIG. 1 and, in FIG. 7, each of the elastic members 20 consists of two elastic elements and such elastic members 20 are attached to the outer sheet 401b intermittently in the fourth machine direction $MD_4$. Then the inner sheet 401a is laminated with the outer sheet 401b. In the fifteenth step 515, the first composites 305 are placed upon and bonded to the inner sheet 401a between each pair of the adjacent elastic members 20, 20 to obtain the fourth continuous assembly 402. Such fourth continuous assembly 402 including the elastic members 20 may be utilized to attach the waist elastic member 20 to the diaper 1 obtained through the manufacturing processes illustrated by FIGS. 5 and 6.

Figure 8:
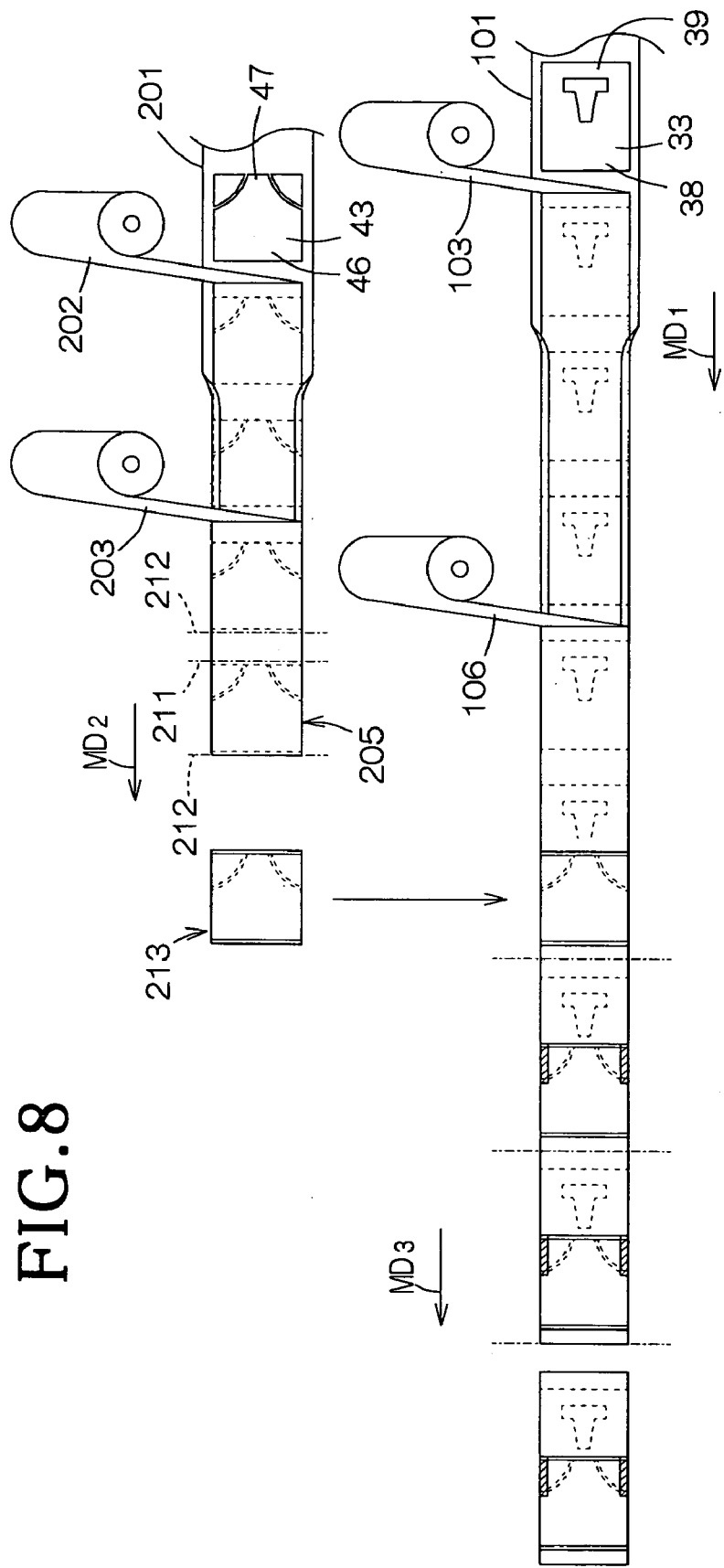
FIG. 8 is a diagram partially illustrating the process according to still another preferred embodiment of the invention.
Figure 9:
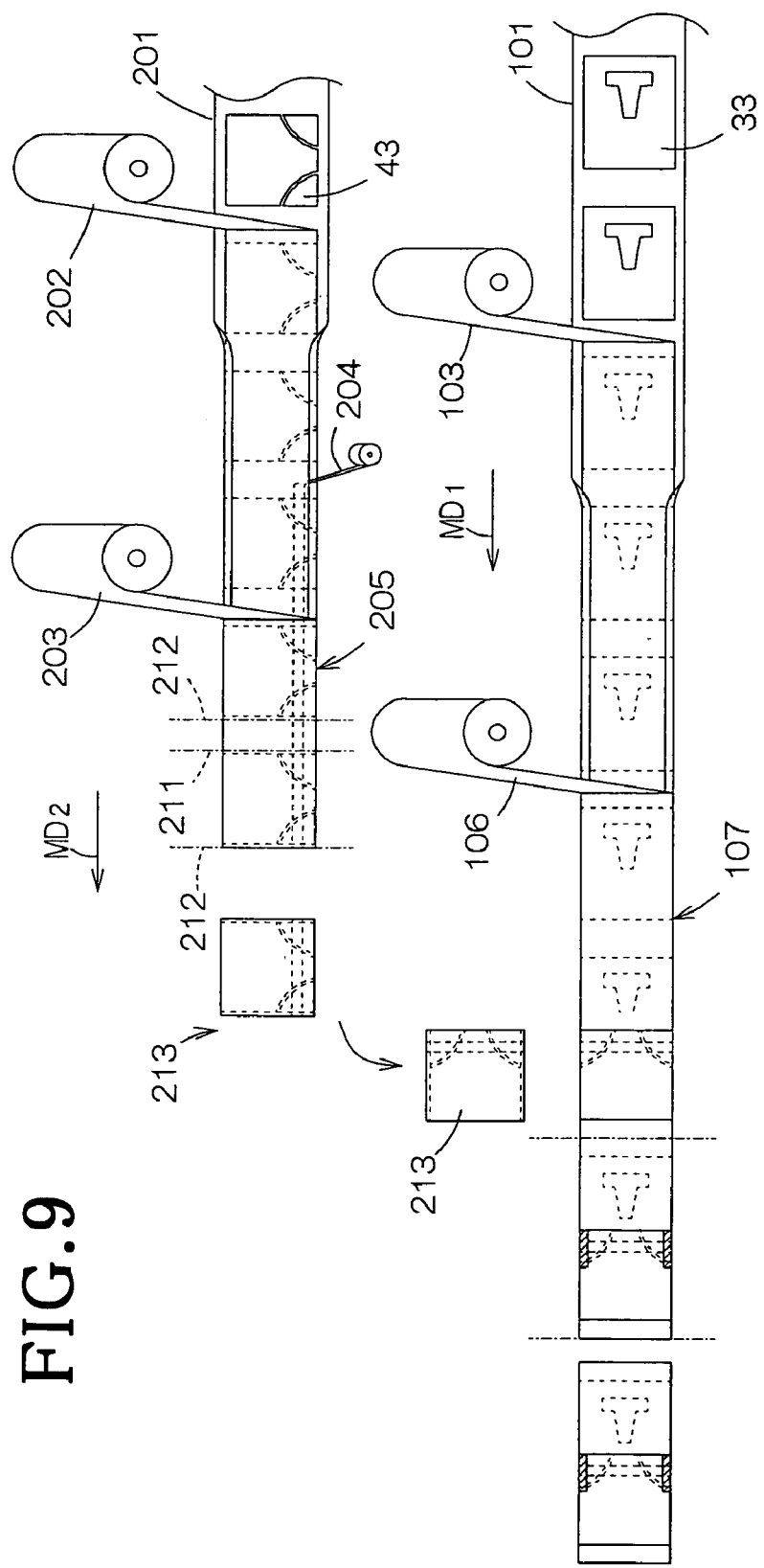
FIG. 9 is a diagram partially illustrating the process according to further another preferred embodiment of the invention.

FIG. 8 illustrates a part of the manufacturing process according to one preferred embodiment of the invention comprising the steps similar to those in FIG. 5. In the manufacturing process illustrated herein, the front section 38 and the rear section 39 of the first core 33 are oriented in the first machine direction $MD_1$ when the first core 33 is placed on the first continuous nonwoven fabric web 101 running in the first machine direction $MD_1$. Similarly, the front section 46 and the rear section 47 of the second core 43 are oriented in the second machine direction $MD_2$ when the second core 43 is placed on the second continuous nonwoven fabric web 201 running in the second machine direction $MD_2$. In this manufacturing process, a plurality of mechanical devices substantially horizontalized in the first machine direction $MD_1$ and a plurality of mechanical devices substantially horizontalized in the second machine direction $MD_2$ may be installed above and below so that these two machine directions $MD_1$, $MD_2$ may flow into each other from above and below to reduce a transverse space of the plant for making the diaper.

FIG. 8 also illustrates a part of the manufacturing process according to one preferred embodiment of the invention comprising the steps similar to those in FIG. 5. In the manufacturing process illustrated herein, the continuous nonwoven fabric web 101 and the first core 33 run in the first machine direction $MD_1$ in the same manner as in FIG. 8. The second continuous nonwoven fabric web 201 and the second core 43 run in the second machine direction $MD_2$ in the same manner as in FIG. 5. In the second machine direction $MD_2$, the second continuous assembly 205 is successively cut along the cutting lines 211, 212 comprising the second core 43 and the second body fluid spreadable sheet 202 sandwiched between the second continuous nonwoven fabric web 201 and the second continuous liquid-pervious sheet 203 to obtain the second panel precursors 213. This second panel precursors 213 are turned by an angle of 90° and then these second panel precursors 213 are placed on the second continuous assembly 107 running in the first machine direction $MD_1$. As in the case of FIG. 5, such manufacturing process facilitates the continuous spacer 204 to be continuously fed and facilitates also the rubber thread extending in the circumferential direction of the waist such as the waist elastic member 20 to be continuously fed to the second panel precursor 213.

Figure 10:
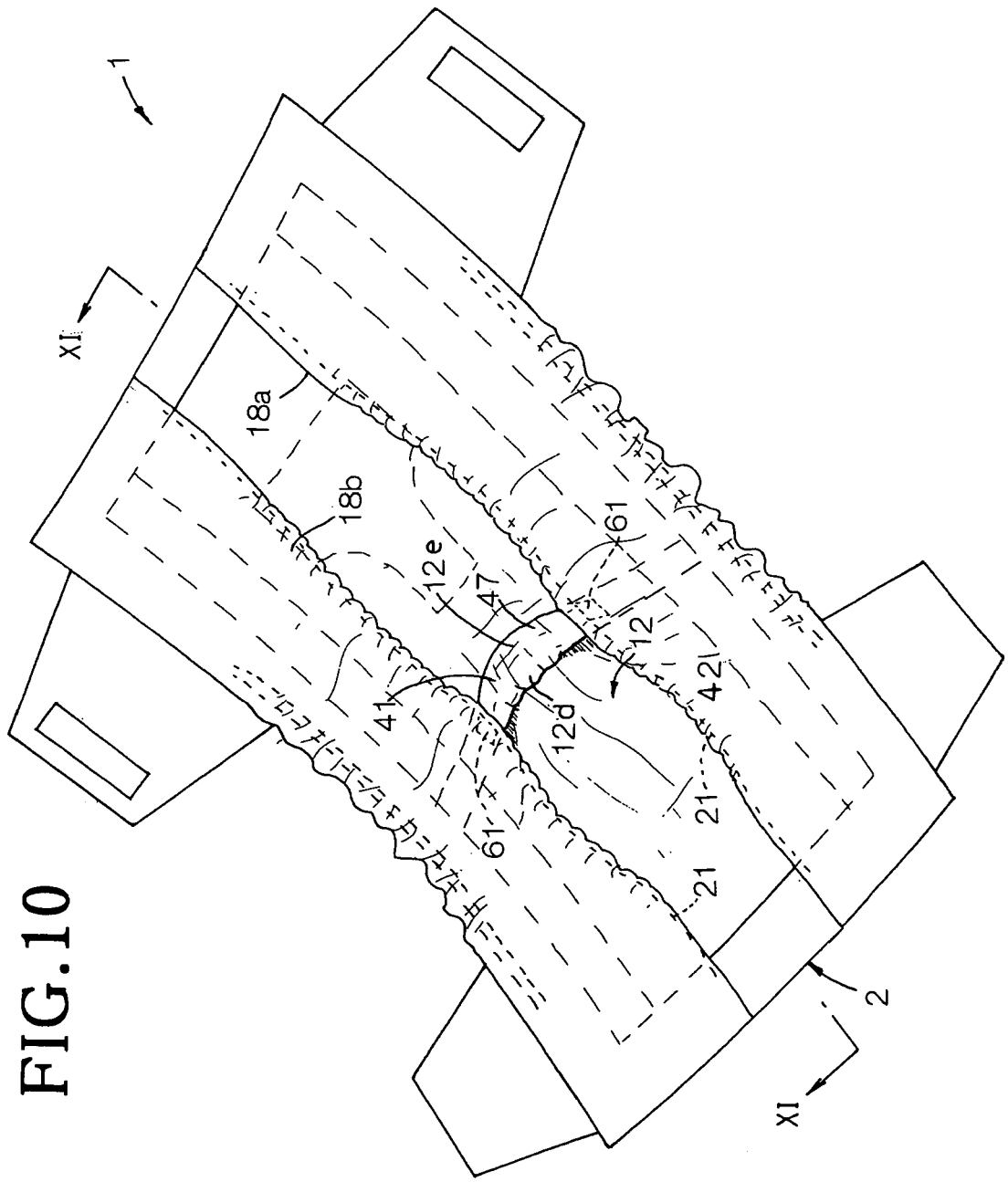
FIG. 10 is a perspective view showing a diaper constructed in a manner different from the diaper of FIG. 1.
Figure 11:
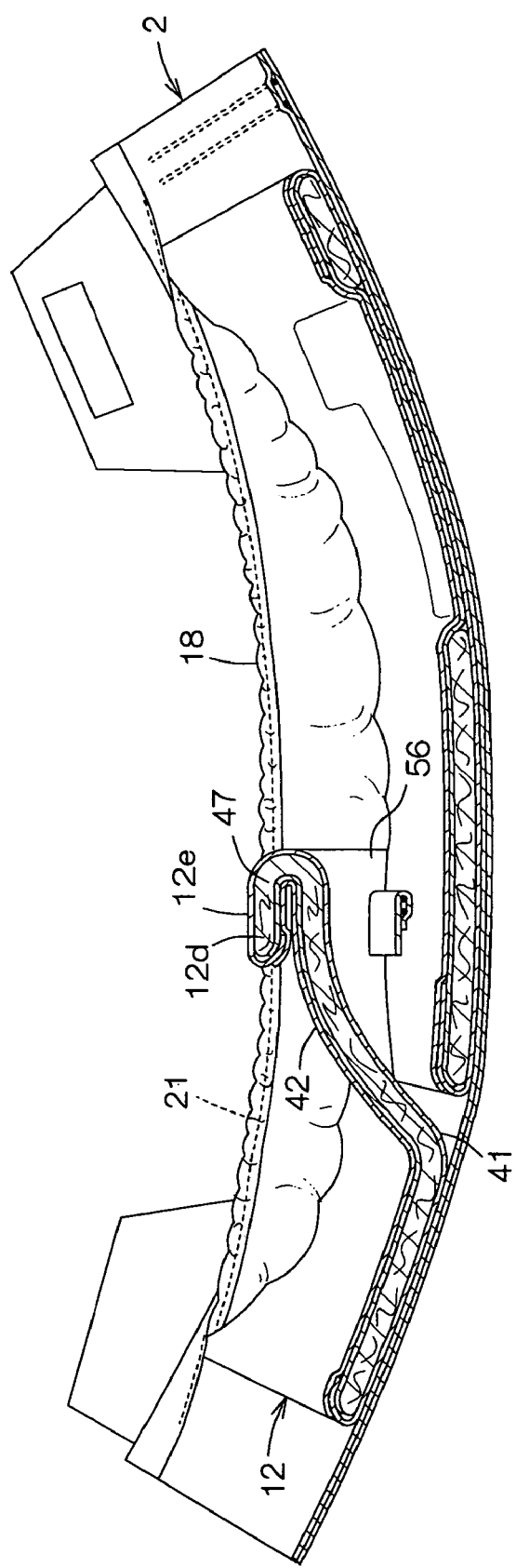
FIG. 11 is a sectional view taken along the line XI—XI in FIG. 10.

FIG. 10 is a perspective view showing a diaper 1 similar to the diaper 1 of FIG. 1 and FIG. 11 is a sectional view taken along a line XI—XI in FIG. 10. In this diaper 1, the rear section 47 of the second panel 12 is partially folded back so that the second inner sheet 42 constituting the second panel 12 is folded back face to face in this folded back segment 12d. In the fold 12d, the second outer sheet 41 is exposed outside the pocket 56. The leak-barrier cuffs 13 are respectively bonded at the regions 61 thereof to the second outer sheet 41 in the fold 12d. The leak-barrier cuffs 13 move upward from the panel-like component 2 so as to rise thereon under contractile force of the elastic members 21 as the diaper 1 is put on the wearer's body and consequently further bows. Thereupon, the portion of the rear section 47 of the second panel 12 forming the fold 12d and the pocket 56 is lifted by the cuffs 13. A top 12e of the fold 12d lifted in this manner is adapted to come in contact with the wearer's skin between the genital organ and the anus so that the fold 12d may function to block loose passage flowing forward as well as urine flowing rearward. Such fold 12d in the diaper 1 can be formed by folding back the desired regions of the first continuous assembly 205 in the course defined between the ninth step 509 and the tenth step 510 in the manufacturing process illustrated by FIG. 5.

The method for making the diaper according to this invention is capable of continuous production of the disposable diaper having the feces retaining pocket formed by overlapping the first and second panels each other in the vicinity of the crotch region improved so that this pocket can be widely opened by spacing these first and second panels from each other.

What is claimed is:

1. A method for continuously making disposable diapers, each said disposable diaper defining a front waist region, a rear waist region and a crotch region extending between these two waist regions, said disposable diaper having a longitudinal direction, a transverse direction and a thickness direction and comprising a liquid-impervious sheet having a first inner surface and a first outer surface opposite to said first inner surface, a first body absorbent panel lying on the side of said first inner surface and having a second outer surface facing said first inner surface and a second inner surface opposite to said second outer surface, said first body fluid absorbent panel extending in said longitudinal direction over at least said rear waist region and said crotch region, and a second body fluid absorbent panel having a third outer surface facing at least a part of said second inner surface and a third inner surface opposite to said third outer surface, said second body fluid absorbent panel extending in said longitudinal direction over said front waist region and said crotch region but not to said rear waist region so that said second body fluid absorbent panel overlaps said first body fluid absorbent panel in said crotch region, wherein said second body fluid absorbent panel is bonded along its transversely opposite side edges to one of said liquid-impervious sheet and said first body fluid absorbent panel so that a region of said second body fluid absorbent panel defined between said transversely opposite side edges is spaced from said first body fluid absorbent panel in said thickness direction, said method for comprising forming said second body fluid absorbent panel to be spaced from said first body fluid absorbent panel through a manufacturing process comprising the steps of:

(1) continuously feeding a first nonwoven fabric web destined to form said first body fluid absorbent panel in a first machine direction;

(2) placing first body fluid absorbent cores on an inner surface of said first nonwoven fabric web, which has said inner surface and an outer surface, intermittently in said first machine direction;

(3) continuously feeding a first liquid-pervious sheet in said first machine direction so that said first cores are sandwiched between said first liquid-pervious sheet and said first nonwoven fabric web to form a first continuous assembly comprising a plurality of said first body fluid panels connected one with another in said first machine direction;

(4) continuously feeding a second nonwoven fabric web destined to form said second body fluid absorbent panel in a second machine direction;

(5) placing second body fluid absorbent cores on an inner surface of said second nonwoven fabric web which has said inner surface and an outer surface, intermittently in said second machine direction;

(6) continuously feeding a second liquid-pervious sheet in said second machine direction so that said second cores are sandwiched between said second liquid-pervious sheet and said second nonwoven fabric web to form a second continuous assembly comprising a plurality of said second body fluid panels connected one with another in said second machine direction;

(7) feeding said first and second continuous assemblies in a third machine direction which is an extension of the first and second machine directions so that said first liquid-pervious sheet and said second nonwoven fabric web face each other, the first cores and second cores are in positions mutually aligned in the third machine direction and said first and second continuous assemblies overlap each other in a cross direction crossing said third machine direction;

(8) bonding respective overlapping sections of said first and second continuous assemblies to each other in the vicinity of transversely opposite side edges of said second cores as viewed in said third machine direction to obtain a third continuous assembly;

(9) successively cutting said third continuous assembly along cutting lines extending in said cross direction to obtain a plurality of first composites each including one of said first cores as well as one of said second cores and first and second edges extending in parallel to each other and defined by one pair of said cutting lines;

(10) continuously feeding a first liquid-impervious sheet having inner and outer surfaces in a fourth machine direction and placing said first composites one by one on said first liquid-impervious sheet with said first nonwoven fabric web as well as said second nonwoven fabric web facing said inner surface of said first liquid-impervious sheet, and then bonding respective peripheral edges of said first composites to said first liquid-impervious sheet to obtain a fourth continuous assembly;

(11) bonding a pair of continuous leak-barrier cuffs each having first and second side edges extending in parallel to each other, said second side edges made of belt-like material being elastically stretchable and contractable in a longitudinal direction thereof, along said first side edges to said fourth continuous assembly with said second side edges of said cuffs being stretched, in the vicinity of said first and second edges of said first composites attached to said fourth continuous assembly;

(12) placing said continuous cuffs bonded to said fourth continuous assembly in the vicinity of said first edge and said continuous cuffs bonded to said fourth continuous assembly in the vicinity of said second edge upon said first liquid-pervious sheet and said second liquid-pervious sheet with said second side edges of said cuffs facing each other and then bonding said continuous cuffs to said first composites in the vicinity of respective ends crossing said first and second edges;

(13) partially bonding said second side edges of respective said continuous cuffs to said second liquid-pervious sheet in an intermediate region of the fourth continuous assembly as viewed in a cross direction crossing the fourth machine direction to cause said first and second body fluid absorbent panels to be spaced from each other; and

(14) following said step (13), successively cutting said fourth continuous assembly along a line defined between each pair of adjacent said first composites to obtain individual said diapers or precursors of said individual diapers.

2. The method as defined by claim 1, wherein said first liquid-impervious sheet comprises a liquid-impervious plastic film and a nonwoven fabric layer laminated on at least one of inner and outer surfaces of said film.

3. The method as defined by claim 1, wherein said belt-like material comprises a nonwoven fabric layer and rubber thread attached in stretched state to said nonwoven fabric layer.

4. The method as defined by claim 1, wherein said first machine direction and said second machine direction coincide with a transverse direction of said first liquid-impervious sheet while said fourth machine direction coincides with said longitudinal direction of said first liquid-impervious sheet and each said first composite is placed upon said first liquid-impervious sheet after said first composite has been turned 90°.

5. The method as defined by claim 4, wherein said step (6) is followed by said step (7) in which said second continuous assembly placed upon said first continuous assembly is partially folded back along folding guide lines extending in parallel to said second machine direction so that said second liquid-pervious sheet overlaps itself and said second nonwoven fabric web constituting said second continuous assembly faces said continuous cuffs and, in said step (13), said second side edges of said continuous cuffs are partially bonded to said second nonwoven fabric web instead of said second liquid-pervious sheet.

6. The method as defined by claim 1, wherein said first machine direction and said second machine direction coincide with the longitudinal direction of said first liquid-impervious sheet.

7. The method as defined by claim 1, wherein said first machine direction coincides with the longitudinal direction of said first liquid-impervious sheet while said second machine direction coincides with the transverse direction of said first liquid-impervious sheet, and said method further includes turning each said first body fluid absorbent panel obtained by cutting said first continuous assembly or each said second body fluid absorbent panel obtained by cutting said second continuous assembly 90°.

8. The method as defined by claim 1, further including attaching, in stretched state, a continuous spacer made of belt-like elastic material to said first or second continuous assembly for reducing a width of said diaper in said crotch region, thereby causing said first and second body fluid absorbent panels to be spaced from each other.

9. A method for continuously making disposable diapers, each said disposable diaper defining a front waist region, a rear waist region and a crotch region extending between these two waist regions, said disposable diaper having a longitudinal direction, a transverse direction and a thickness direction and comprising a liquid-impervious sheet having a first inner surface and a first outer surface opposite to said first inner surface, a first body absorbent panel lying on the side of said first inner surface and having a second outer surface facing said first inner surface and a second inner surface opposite to said second outer surface, said first body fluid absorbent panel extending in said longitudinal direction over at least said rear waist region and said crotch region, and a second body fluid absorbent panel having a third outer surface facing at least a part of said second inner surface and a third inner surface opposite to said third outer surface, said second body fluid absorbent panel extending in said longitudinal direction over said front waist region and said crotch region but not to said rear waist region so that said second body fluid absorbent panel overlaps said first body fluid absorbent panel in said crotch region, wherein said second body fluid absorbent panel is bonded along its transversely opposite side edges to one of said liquid-impervious sheet and said first body fluid absorbent panel so that a region of said second body fluid absorbent panel defined between said transversely opposite side edges is spaced from said first body fluid absorbent panel in said thickness direction, said method comprising forming said second body fluid absorbent panel to be spaced from said first body fluid absorbent panel through a manufacturing process comprising the steps of:

(1) continuously feeding a first nonwoven fabric web destined to form said first body fluid absorbent panel in a first machine direction;

(2) placing first body fluid absorbent cores on an inner surface of said first nonwoven fabric web, which has said inner surface and an outer surface intermittently in said first machine direction;

(3) continuously feeding a first liquid-pervious sheet in said first machine direction so that said first cores are sandwiched between said first liquid-pervious sheet and said first nonwoven fabric web to form a first continuous assembly comprising a plurality of said first body fluid panels connected one with another in said first machine direction;

(4) continuously feeding a second nonwoven fabric web destined to form said second body fluid absorbent panel in a second machine direction;

(5) placing second body fluid absorbent cores on an inner surface of said second nonwoven fabric web, which has said inner surface and an outer surface, intermittently in said second machine direction;

(6) continuously feeding a second liquid-pervious sheet in said second machine direction so that said second cores are sandwiched between said second liquid-pervious sheet and said second nonwoven fabric web to form a second continuous assembly comprising a plurality of said second body fluid panels connected one with another in said second machine direction;

(7) feeding a continuous spacer made of belt-like elastic material, in stretched state, in said first machine direction or in said second machine direction so that said continuous spacer straddles said first cores in said first continuous assembly or said second cores in said second continuous assembly, and bonding said continuous spacer to said first liquid-pervious sheet in said first continuous assembly or said second nonwoven fabric web in said second continuous assembly (8) feeding said first and second continuous assemblies in a third machine direction which is an extension of the first and second machine directions so that said first liquid-pervious sheet and said second nonwoven fabric web face each other, the first cores and second cores are in corresponding positions in the third machine direction and said first and second continuous assemblies overlap each other in a cross direction crossing said third machine direction;

(9) bonding respective overlapping sections of said first and second continuous assemblies to each other in the vicinity of transversely opposite side edges of said second cores as viewed in said third machine direction to obtain a third continuous assembly

(10) successively cutting said third continuous assembly along cutting lines extending in said cross direction to obtain a plurality of first composites each including one of said first cores as well as one of said second cores and first and second edges extending in parallel to each other and defined by one pair of said cutting lines;

(11) continuously feeding a first liquid-impervious sheet having inner and outer surfaces in a fourth machine direction and placing said first composites one by one on said first liquid-impervious sheet with said first nonwoven fabric web as well as said second nonwoven fabric web facing said inner surface of said first liquid-impervious sheet, and then bonding respective peripheral edges of said first composites to said first liquid-impervious sheet to obtain a fourth continuous assembly; and

(12) following said step (11), successively cutting said fourth continuous assembly along a line defined between each pair of adjacent said first composites to obtain individual said diapers or precursors of said individual diapers.

10. The method as defined by claim 9, wherein said first liquid-impervious sheet comprises a liquid-impervious plastic film and a nonwoven fabric layer laminated on at least one of inner and outer surfaces of said film.

11. The method as defined by claim 9, wherein said first machine direction and said second machine direction coincide with a transverse direction of said first liquid-impervious sheet while said fourth machine direction coincides with said longitudinal direction of said first liquid-impervious sheet and each said first composite is placed upon said first liquid-impervious sheet after said first composite has been turned 90°.

12. The method as defined by claim 9, wherein said first machine direction and said second machine direction coincide with the longitudinal direction of said first liquid-impervious sheet.

13. The method as defined by claim 9, wherein said first machine direction coincides with the longitudinal direction of said first liquid-impervious sheet while said second machine direction coincides with the transverse direction of said first liquid-impervious sheet, and said method further includes turning each said first body fluid absorbent panel obtained by cutting said first continuous assembly or each said second body fluid absorbent panel obtained by cutting said second continuous assembly 90°.

14. The method as defined by claim 9, further including bonding a pair of continuous leak-barrier cuffs each having first and second side edges extending in parallel to each other, said second side edges made of belt-like material being elastically stretchable- and contractable in a longitudinal direction thereof, along said first side edges to said fourth continuous assembly with said second side edges of said cuffs being stretched, in the vicinity of said first and second edges of said first composites attached to said fourth continuous assembly.

15. The method as defined by claim 14, further including a partially bonding said continuous cuffs to any one of said second liquid-pervious sheet and said second nonwoven fabric web sandwiching said second cores.

16. A method for continuously making disposable diapers, each said disposable diaper defining a front waist region, a rear waist region and a crotch region extending between these two waist regions, said disposable diaper having a longitudinal direction, a transverse direction and a thickness direction and comprising a liquid-impervious sheet having a first inner surface and a first outer surface opposite to said first inner surface, a first body absorbent panel lying on the side of said first inner surface and having a second outer surface facing said first inner surface and a second inner surface opposite to said second outer surface, said first body fluid absorbent panel extending in said longitudinal direction over at least said rear waist region and said crotch region, and a second body fluid absorbent panel having a third outer surface facing at least a part of said second inner surface and a third inner surface opposite to said third outer surface, said second body fluid absorbent panel extending in said longitudinal direction over said front waist region and said crotch region but not to said rear waist region so that said second body fluid absorbent panel overlaps said first body fluid absorbent panel in said crotch region, wherein said second body fluid absorbent panel is bonded along its transversely opposite side edges to one of said liquid-impervious sheet and said first body fluid absorbent panel so that a region of said second body fluid absorbent panel defined between said transversely opposite side edges is spaced from said first body fluid absorbent panel in said thickness direction, said method comprising forming said second body fluid absorbent panel to be spaced from said first body fluid absorbent panel through a manufacturing process comprising the steps of:

(1) continuously feeding said liquid-impervious sheet having said first inner surface and said first outer surface in a first machine direction;

(2) attaching said first body fluid absorbent panels to said first inner surface of said continuously fed liquid-impervious sheet so that each of said first body fluid absorbent panels extends at least over a section allocated for said rear waist and crotch regions;

(3) placing said second body fluid absorbent panels on said continuously fed liquid-impervious sheet so that each of said second body fluid absorbent panels extends over a section of said continuously fed liquid-impervious sheet allocated for said front waist and crotch regions and said second outer surface of said second body fluid absorbent panel faces said first inner surface of the respective first body fluid absorbent panel in said crotch region, and then bonding, in said crotch region, said transversely opposite edges of each said second body fluid absorbent panel to transversely opposite side edges of the respective first body fluid absorbent panel or to transversely opposite side edges of said continuously fed liquid-impervious sheet extending outside said transversely opposite side edges of said first body fluid absorbent panel;

(4) feeding, in stretched state, a pair of leak-barrier cuff members formed by belt-like material extending from said section allocated for said crotch region to said sections allocated for said front and rear waist regions, said belt-like material being elastically stretchable and contractable in a direction in which said belt-like material extends and having inner and outer side edges, toward said continuously fed liquid-impervious sheet having said first and second body fluid absorbent panels attached thereto, then, in said crotch regions, attaching said outer side edges of said respective cuff members to said continuously fed liquid-impervious sheet in regions outside respective said side edges of said first and second body fluid absorbent panels, and covering edges of said first and second body fluid absorbent panels with said inner side edges of respective said cuff members; and (5) causing said second body fluid absorbent panel to be spaced from the respective first body fluid absorbent panel by at least one of substeps a) and b) as follows:
 a. bonding, in each section of said continuously fed liquid-impervious sheet allocated for said crotch region, portions of said inner side edges of said leak-barrier cuff members in stretched state to the portions of said second body fluid absorbent panel covered with said portions of said inner side edges; and b. attaching, in each section of said continuously fed liquid-impervious sheet allocated for said crotch region, a belt-like elastic spacer transversely extending in stretched state between said first and second body fluid absorbent panels to said side edges of at least one of said first and second body fluid absorbent panels.

* * * * *